United States Patent [19]

Del Pesco et al.

[11] 4,059,628
[45] Nov. 22, 1977

[54] PREPARATION OF AROMATIC AMINES

[75] Inventors: Thomas Wayne Del Pesco; Frank Julian Weigert, both of Wilmington, Del.

[73] Assignee: E. I. Du Pont de Nemours and Company, Wilmington, Del.

[21] Appl. No.: 687,175

[22] Filed: May 17, 1976

Related U.S. Application Data

[63] Continuation-in-part of Ser. No. 536,584, Dec. 26, 1974, abandoned, which is a continuation-in-part of Ser. No. 445,914, Feb. 26, 1974, abandoned.

[51] Int. Cl.$^2$ ............... C07C 85/18; C07C 85/24
[52] U.S. Cl. ............. 260/581; 252/437; 252/439; 252/461; 252/462; 252/463; 252/464; 252/465; 252/466 J; 252/469; 252/471; 252/472; 252/475; 252/476; 252/468; 252/470
[58] Field of Search ............................ 260/581

[56] References Cited

U.S. PATENT DOCUMENTS

| | | | |
|---|---|---|---|
| 2,486,934 | 11/1949 | Erchak | 260/465 C |
| 2,948,755 | 8/1960 | Schmerling | 260/581 |
| 2,980,735 | 4/1961 | Bloch | 260/578 |
| 3,254,023 | 5/1966 | Miale et al. | 208/120 |
| 3,347,921 | 10/1967 | Carrubba et al. | 260/581 |
| 3,361,818 | 1/1968 | Barker | 260/578 |
| 3,442,950 | 5/1969 | Barker | 260/576 |
| 3,553,268 | 1/1971 | Solomon et al. | 260/581 |
| 3,919,155 | 11/1975 | Squire | 260/571 |
| 3,929,889 | 12/1975 | Squire | 260/571 |

FOREIGN PATENT DOCUMENTS

| | | | |
|---|---|---|---|
| 815,064 | 6/1969 | Canada | 260/581 |
| 453,546 | 12/1948 | Canada | 260/581 |
| 48-15837 | 2/1973 | Japan | 260/581 |

OTHER PUBLICATIONS

Plate et al., Vestnik Moscow University, vol. 10, No. 2, pp. 77–80, (1955).

*Primary Examiner*—Daniel E. Wyman
*Assistant Examiner*—John J. Doll
*Attorney, Agent, or Firm*—Anthony P. Mentis

[57] ABSTRACT

Aniline and alkyl anilines are obtained by the reaction of anhydrous ammonia with cyclohexane or cyclohexane having up to two lower alkyl substituents at elevated temperatures, such as 300–650° C, in the presence of selected catalysts such as zinc oxide alone or with vanadium, molybdenum, or titanium oxides, etc.; metal compounds such as vanadates, molybdates and titanates; and cadmium sulfide, zinc selenide and the like.

38 Claims, No Drawings

PREPARATION OF AROMATIC AMINES

CROSS-REFERENCE TO RELATED APPLICATIONS

This application is a continuation-in-part of application Ser. No. 536,584 filed Dec. 26, 1974, now abandoned, which is a continuation-in-part of application Ser. No. 449,914 filed Feb. 26, 1974, now abandoned.

BACKGROUND OF THE INVENTION

1. Field of the Invention

Aniline and alkyl anilines are obtained by the reaction of anhydrous ammonia with cyclohexane or cyclohexane having up to two lower alkyl substituents at elevated temperatures, such as 300°–650° C, in the presence of selected catalysts, such as zinc oxide alone or with vanadium, molybdenum or titanium oxides, etc.; metal compounds such as vanadates, molybdates and titanates; and cadmium sulfide, zinc selenide and the like.

2. Description of the Prior Art

Aniline has been prepared by reduction of nitrobenzene or by ammonolysis of chlorobenzene. Other methods of producing aniline are also known. For example, a noncatalytic method reacts cyclohexane, ammonia and sulfur, as shown in Canadian Pat. No. 815,064.

A catalytic method is shown in Bloch, U.S. Pat. No. 2,980,735 where an alkyl cyclopentene is heated in the presence of a catalyst comprising a Group VIII metal such as Co or Ni on an acidic support (e.g. $Al_2O_3$) with oxides of metals of Groups V, VI and VII.

None of the prior art, however, discloses the catalytic production of aniline from only cyclohexane and ammonia using certain selected metal oxides or metal sulfides, etc., as catalysts.

DESCRIPTION OF THE INVENTION

The invention is the discovery of the process which consists essentially in heating a starting hydrocarbon of the formula

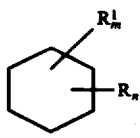

wherein R and $R^1$ are alkyl of 1–4 carbon atoms and $m$ and $n$ individually are 0 or 1, with anhydrous ammonia at a temperature of 300°–650° C to produce a compound of the formula

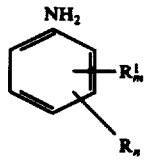

where $R^1$, R, $m$ and $n$ have the values stated above, and where the heating is carried out in the presence of a catalyst selected from the group consisting of:

A. one or more oxides of Al, Cd, Ce, Fe, In, Sn, Th, Ti, Zn and Zr;

B. vanadium oxide and one or more oxides of Ag, As, Ba, Ca, Cd, Ce, Co, Cu, Eu, Fe, Gd, Hf, In, La, Mg, Mn, Ni, P, Pb, Sb, Sn, Sr, Ti, U and Zn;

C. titanium oxide and one or more oxides of Bi, Cr, Cu, Mo, Pb, U and W;

D. zinc oxide and one or more oxides of Cr, La, Mg, P, Si, Sb, W and the pair Bi-Mo;

E. aluminum oxide and one or more oxides of Cu, Eu, La, Mn, Pb and U;

F. aluminum oxide, molybdenum oxide and one or more oxides of Ca, Cd, Ce, Cu, Er, Fe, In, La, Ni, Pb, Sm, Sr, Ti, U, Y and Zn;

G. aluminum oxide, tungsten oxide and one or more oxides of Ca, Ce, Cu, Fe, In, La, Pb, Sm, Ti, U and Zn;

H. aluminum oxide, titanium oxide and one or more oxides of Cr, Mg, rare earths, Re, Te and V;

I. aluminum oxide, titanium oxide, zinc oxide and one or more oxides of Ag, Bi, Ca, Co, Cr, Cu, Hg, La, Mg, Nb, Ni, Pb, Pr, Ru, Sm, Sr, V, Yb and Y;

J. aluminum oxide, molybdenum oxide, bismuth oxide and one or more oxides of Ca, Cu, Pb, Ti and Zn;

K. aluminum oxide, molybdenum oxide, zirconium oxide and one or more oxides of Ce, Ti and Zn;

L. molybdenum oxide and one or more oxides of Cd, Ce, Cu, Fe, Gd, La, Mg, Mn, Nb, P, Pb, Ti and Zn;

M. zinc oxide, titanium oxide and one or more oxides of Cr, La, Mg and Nb;

N. CdS; CoS; CdS/aluminum oxide; CdS/titanium oxide/aluminum oxide; chromium sulfide; ZnSe; ZnS; ZnTe; ZnS/aluminum oxide; CdS/ZnS/aluminum oxide; and $WS_2$; and O. aluminum oxide, vanadium oxide and one or more oxides of Ag, Ba, Ca, Cd, Cu, Ga, In, La, Mg, Pb, Sr, Y, Zn and Zr.

The reaction may be depicted as

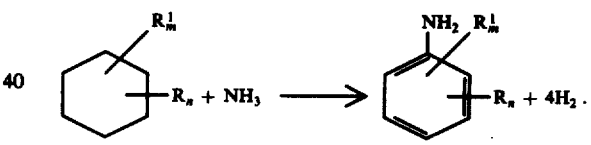

The term "oxide" includes binary oxides, ternary oxides, quaternary oxides and higher polynary oxides as well as solid solutions and nonstoichiometric oxides. It includes a single oxide; mixed oxides of a single metal in different valence states such as FeO and $Fe_2O_3$, etc.; and mixed oxides of different metals such as physical mixtures of zinc oxide and aluminum oxide, etc., and also oxides such as $Zn_3V_2O_8$, $Bi_4ZnMo_3O_{16}$, $CdSnO_3$ and the like. The invention is a broad one in that all combinations of the metal compounds, as set out in the groups above, are operative. The compounds can be used in all proportions. It is advantageous that a member of group A or vanadium oxide comprises half or more of the catalyst.

Preferred for their ability to convert cyclohexane to aniline are catalysts containing zinc oxide and titanium oxide and catalysts containing zinc oxide and vanadium oxide. In each of these combinations one or more of the other metal compounds of the invention can be present.

A group of catalysts preferred for their ability to produce aniline with fewer by-products comprises zinc oxide/titanium oxide and zinc oxide/vanadium oxide catalysts each including one or more oxides of the group aluminum, cadmium, cerium, lanthanum and thorium.

A still further group of catalysts, preferred because of their long life, comprises aluminum oxide/molybdenum oxide including one or more of calcium oxide, lead oxide and rare earth oxides.

In addition to cyclohexane itself, alkyl cyclohexanes having up to 2 alkyl groups having no more than 4 carbons in each alkyl can be used. These include methylcyclohexane, ethylcyclohexane, n-butylcyclohexane, 1,2-dimethylcyclohexane, 1,4-dimethylcyclohexane, 1,3-di-n-butylcyclohexane and 1,4-diethylcyclohexane. All of these starting hydrocarbons are generally immiscible with water and are anhydrous when employed.

Although temperatures in the range of 300°–650° C are employed, the specific optimum temperature is dependent upon the particular catalyst used and on other conditions such as pressure, contact time, and ratio of reactants. Preferred, however, is 400°–600°; more preferred is the range of 450°–550° which generally gives the highest yields and conversions.

The molar ratio of the hydrocarbon compound to ammonia can vary from 1/100 to 10/1. A preferred range is 5/1 to 1/10.

The reaction can be carried out at any pressure but pressures in the range of 0.5 to 20 atmospheres are presently preferred.

The aromatic amine is produced when the reactants make physical contact with the catalyst at the reaction temperature. Accordingly any amount of catalyst can be used since it merely needs to be present in order for the reaction to occur and may be simply designated as a catalytically effective amount. The time during which the reactants are in contact with the catalyst at the reaction temperature is the contact time and can vary over a wide range. For economic operation it can range from about 0.1 second to about 10 minutes. A preferred range is about 1 second to about 8 minutes.

The reaction does not require oxygen and air need not be present. The reaction can be carried out in air but because of the known tendency of cyclohexane and aniline to react with oxygen it is generally best to proceed in the absence of air. This gives higher yields of aniline and fewer by-products and can be accomplished by carrying out the reaction in an atmosphere which contains only the cyclohexane hydrocarbon and gaseous ammonia. Optionally an inert gas such as nitrogen, helium, argon, neon or the like can be present. A convenient method by which oxygen may be excluded from the system is to simply pass a stream of gaseous ammonia and starting hydrocarbon through the reactor containing the catalyst to flush out any contained air prior to heating the catalyst and reactants to start the reaction.

Combinations of catalysts are especially useful in providing desired activity, selectivity, increased life. and the like. Relatively inert catalyst carriers or diluents can be present, e.g. carbon, silicon carbide, silica, magnesia, boron phosphate, and the like, as known in the art.

The catalysts can be made by any conventional or suitable method known in the art. For example, these methods include direct heating of the elements in air to form the oxides. Other methods include evaporation, impregnation or precipitation, each followed by calcination.

In the precipitation method, aqueous solutions of the desired constituents are mixed with a solution of a precipitating agent. A variety of bases or base forming compounds can be used as for example aqueous ammonia, ammonium carbonate, ammonium bicarbonate, urea and the like. The presence of impurities in the final catalyst is minimized by carrying out the precipitating with dilute solutions and by using ammonia or ammonia salts as the precipitant along with nitrates of the desired metals. The resulting precipitate then requires a minimum of washing since any adsorbed material remaining can be removed in the subsequent calcination step. The use of nitrates is recommended since other anions such as sulfate or halide generally act as catalyst poisons. Where a metal halide or sulfate is used, it is important to wash the precipitated material thoroughly to remove such deleterious ions.

In the impregnation method, a solution of an active component or components is contacted with a support to thoroughly wet it. An excess of the impregnating solution is generally used and when the support is thoroughly saturated, the excess solution is removed, as by filtration or decantation. The impregnated support is then dried and subjected to calcination. The use of nitrate solutions is also recommended in this method.

In the evaporation method, the desired components are mixed together with water to form a slurry or solution. The water is evaporated and the resultant solid is then dried and calcined. This method is of value where unwanted materials are not present and a washing step is not needed.

In the calcination step which decomposes the salts such as the nitrates or carbonates to the oxides, the catalyst material is heated in air to a temperature which is generally below 800° C. The calcination is usually carried out for a period of hours, as, for example, overnight.

While not always applicable, a guiding principle which is generally advantageous is to prepare the catalyst with as large a surface area as possible.

In the catalyst preparation, relatively small amounts of other metals from the main groups of the Periodic Table or one or more of the rare earths can be added as textural promoters, i.e. to prevent undue loss of surface area of the catalyst.

The catalysts can be reactivated by burning off any carbonaceous deposit which may form after use. The burning off can be done, for example, by flushing the reactor and its contained catalyst with heated air, oxygen, or air diluted with an inert gas such as nitrogen, helium or argon, for a suitable time as is known in the art.

The oxides of group A are illustrated by aluminum oxide, cadmium oxide, cerium oxide, iron oxide, indium oxide, tin oxide, thorium oxide, titanium oxide, zinc oxide, zirconium oxide and mixtures of any two or more of them such as aluminum oxide and cadmium oxide; cerium oxide and iron oxide; indium oxide and zirconium oxide; zinc oxide, titanium oxide and aluminum oxide; zinc oxide, cerium oxide, and titanium oxide; iron oxide, titanium oxide and aluminum oxide; zinc oxide, cerium oxide, titanium oxide and aluminum oxide, and the like. Other illustrative oxides include cerium zirconate, cadmium stannate, zinc stannate, ferrous titanate, and the like.

The oxides of group B are illustrated by vanadium oxide together with one or more of silver oxide, barium oxide, calcium oxide, cadmium oxide, cerium oxide, cobalt oxide, copper oxide, europium oxide, iron oxide, gadolinium oxide, hafnium oxide, indium oxide, lanthanum oxide, magnesium oxide, manganese oxide, nickel oxide, phosphorus oxide, lead oxide, antimony oxide, tin oxide, strontium oxide, titanium oxide, uranium oxide and zinc oxide. Additional illustrations include the mixtures vanadium oxide, zinc oxide and cadmium oxide; vanadium oxide, lanthanum oxide and zinc oxide; vanadium oxide, magnesium oxide and zinc oxide; vanadium oxide, copper oxide and arsenic oxide; vanadium oxide, zinc oxide and cerium oxide; vanadium oxide, phosphorus oxide and zinc oxide; vanadium oxide, copper oxide and cerium oxide; vanadium oxide, nickel oxide and tin oxide; hafnium vanadate; europium vanadate; strontium vanadate, gadolinium vanadate; zinc metavanadate; zinc pyrovanadate; and zinc orthovanadate.

The oxides of group C are illustrated by titanium oxide together with one or more of bismuth oxide, chromium oxide, copper oxide, molybdenum oxide, lead oxide, uranium oxide and tungsten oxide. Additional illustrations include titanium oxide, molybdenum oxide and bismuth oxide; and lead titanate and the like.

The oxides of group D are illustrated by zinc oxide together with one or more of chromium oxide, lanthanum oxide, magnesium oxide, phosphorus oxide, silicon oxide, antimony oxide, and tungsten oxide. Also illustrative are the mixtures of zinc oxide, bismuth oxide and molybdenum oxide; and zinc oxide, silicon oxide and magnesium oxide.

The oxides of group E are illustrated by aluminum oxide together with one or more of copper oxide, europium oxide, lanthanum oxide, manganese oxide, lead oxide and uranium oxide.

The oxides of group F are illustrated by aluminum oxide and molybdenum oxide together, with one or more of calcium oxide, cadmium oxide, cerium oxide, copper oxide, erbium oxide, iron oxide, indium oxide, lanthanum oxide, nickel oxide, lead oxide, samarium oxide, strontium oxide, titanium oxide, uranium oxide, yttrium oxide and zinc oxide. Additional illustrations are the mixtures of aluminum oxide, molybdenum oxide, lead oxide and lanthanum oxide; aluminum oxide, molybdenum oxide, lead oxide and cerium oxide; aluminum oxide, molybdenum oxide, calcium oxide and cerium oxide; aluminum oxide, molybdenum oxide, titanium oxide and cerium oxide; aluminum oxide, molybdenum oxide, cerium oxide, titanium oxide and lead oxide; aluminum oxide, molybdenum oxide, lanthanum oxide, titanium oxide and lead oxide; aluminum oxide, molybdenum oxide, cerium oxide, titanium oxide and zinc oxide; and aluminum oxide, molybdenum oxide, cerium oxide, titanium oxide and calcium oxide.

The oxides of group G are illustrated by aluminum oxide and tungsten oxide together, with one or more of calcium oxide, cerium oxide, copper oxide, iron oxide, indium oxide, lanthanum oxide, lead oxide, samarium oxide, titanium oxide, uranium oxide, and zinc oxide.

The oxides of group H are illustrated by aluminum oxide and titanium oxide together, with one or more of chromium oxide, magnesium oxide, rare earths oxides, rhenium oxide, tellurium oxide and vanadium oxide.

The oxides of group I are illustrated by aluminum oxide, titanium oxide and zinc oxide together, with one or more of silver oxide, bismuth oxide, calcium oxide, cobalt oxide, chromium oxide, copper oxide, lanthanum oxide, magnesium oxide, mercury oxide, niobium oxide, nickel oxide, lead oxide, praseodymium oxide, ruthenium oxide, samarium oxide, strontium oxide, vanadium oxide, ytterbium oxide and yttrium oxide.

The oxides of group J are illustrated by aluminum oxide, molybdenum oxide and bismuth oxide together, with one or more of calcium oxide, copper oxide, lead oxide, titanium oxide and zinc oxide. Additional illustrations are the mixtures of aluminum oxide, molybdenum oxide, bismuth oxide, titanium oxide, and lead oxide; aluminum oxide, molybdenum oxide, bismuth oxide, titanium oxide and calcium oxide; and aluminum oxide, molybdenum oxide, bismuth oxide, titanium oxide and zinc oxide.

The oxides of group K are illustrated by aluminum oxide, molybdenum oxide and zirconium oxide together, with one or more of cerium oxide, titanium oxide and zinc oxide. Additional illustrations are the mixtures of aluminum oxide molybdenum oxide, zirconium oxide and cerium oxide; and aluminum oxide, molybdenum oxide, zirconium oxide, cerium oxide and titanium oxide.

The oxides of group L are illustrated by molybdenum oxide together with one or more of cadmium oxide, cerium oxide, copper oxide, iron oxide, gadolinium oxide, lanthanum oxide, magnesium oxide, manganese oxide, niobium oxide, phosphorus oxide, lead oxide, titanium oxide, and zinc oxide. Also illustrative is the mixture of molybdenum oxide, lead oxide and lanthanum oxide. Further illustrations are cadmium molybdate, cerium molybdate, gadolinium molybdate, lanthanum molybdate, magnesium molybdate, manganese molybdate, lead molybdate and zinc molybdate.

The oxides of group M are illustrated by zinc oxide and titanium oxide together, with one or more of chromium oxide, lanthanum oxide, magnesium oxide, and niobium oxide.

The oxides of Group O are illustrated by aluminum oxide and vanadium oxide together, with one or more of silver oxide, barium oxide, calcium oxide, cadmium oxide, copper oxide, gallium oxide, indium oxide, lanthanum oxide, magnesium oxide, lead oxide, strontium oxide, zinc oxide, and zirconium oxide.

SPECIFIC EMBODIMENTS OF THE INVENTION

In the following illustrative examples the ammonia is used in its anhydrous state, the process is continuous, all temperatures are in degrees Centigrade, the contact time is about 2 seconds, and all analyses were done by gas chromatography, unless otherwise stated. In general, the proportions of the catalyst components are in weight percent or molar ratios.

EXAMPLE 1

A granular catalyst comprising 10% $ZnS/Al_2O_3$ was placed in a tubular reactor and the assembly heated to 400° at which time anhydrous ammonia and cyclohexane in a 4/1 molar ratio were introduced. The ammonia was introduced in a stream of nitrogen in a ratio of 2 to 5 and the cyclohexane was introduced into the gas stream by a syringe pump at a rate of 1.2 ml/hour. The temperature was kept at 400° and the entire reaction was carried out in the absence of air. The effluent was collected for about 20 minutes in a trap maintained at 0°. Analysis of the colorless liquid effluent by gas chromatography (GC) revealed the presence of aniline and benzonitrile (see Table I).

At the end of the first 20 minute reaction period at 400°, the feed of cyclohexane and ammonia was stopped and the reactor and its contained catalyst were heated to 500°. The feed was then reinstituted and reaction at 500° was carried out for a similar period of about 20 minutes, the effluent being collected in another 0° trap and analyzed by GC.

EXAMPLE 2

The procedure of Example 1 was repeated using 24% ZnO/Al$_2$O$_3$ (Harshaw Zn-0701) as the catalyst.

The products obtained in Examples 1 and 2 were analyzed by gas chromatography carried out by using 20% of a mixture comprising 50% trifluoropropyl silicone and 50% methyl silicone (sold as FS-1265 ® by the Dow Chemical Co.) dispersed on 80% of 60/80 mesh diatomaceous earth (sold as GCR ® by Applied Science Co.), at 200° C at a rate of 50 ml/min of helium. The results for Examples 1 and 2 l are given in Table I below in peak heights (mm) for aniline in column (a) and for benzonitrile in column (b), the aniline at 1.9 min and the benzonitrile at 3.0 min.

TABLE I

| Ex- | | Temperature | | | | | |
|---|---|---|---|---|---|---|---|
| | | 400° | | 500° | | 600° | |
| ample | Catalyst | (a) | (b) | (a) | (b) | (a) | (b) |
| 1 | 10% ZnS/Al$_2$O$_3$ | 78 | 300 | 65 | 0 | — | — |
| 2 | 24% ZnO/Al$_2$O$_3$ | 35 | 0 | 130 | 8 | 175 | 113 |

EXAMPLE 3

A catalyst (10.2 g) consisting of mixed oxides in a molar ratio of 0.347 lanthanum, 0.347 molybdenum and 8.82 aluminum was introduced into a 1 inch diameter tubular reactor and heated to 500°. Anhydrous ammonia at a rate of $1.75 \times 10^{-3}$ moles per minute and cyclohexane at a rate of $3.9 \times 10^{-3}$ moles per minute were then fed into the reactor. The molar ratio of ammonia/cyclohexane was 1/2.2. The effluent was collected in a cooled trap and analysis showed it to contain 0.9% aniline, 1.6% benzene and 97.5% cyclohexane.

EXAMPLE 4

Methylcyclohexane (1.2 ml/hr) and ammonia 0.02 l/min. were passed at 550° C. over a catalyst consisting of 24% ZnO/Al$_2$O$_3$ as in Example 3. The products consisted of aniline, benzonitrile and the three isomeric toluidines, the meta compound predominating.

EXAMPLE 5

A catalyst (0.8 g) consisting of mixed oxides in a molar ratio of one of cadmium, twenty of zinc and forty of vanadium was inserted in a reactor and anhydrous ammonia and cyclohexane charged at one atmosphere pressure in the molar ratio of 4 to 1 at a total rate of 60 mmoles per hour. At 550° aniline, collected in a cool trap, was produced at a rate corresponding to 35 mg/g catalyst/hr.

EXAMPLE 6

Catalyst (3.8 g) consisting of an oxide mixture of a molar ratio of 1 of aluminum, 3.8 of titanium, and 1.4 zinc was placed in a reactor and anhydrous ammonia and cyclohexane charged at one atmosphere in the molar ratio of 4 to 1 at a total rate of 60 mmoles/hr. At 450° aniline was produced at a rate corresponding to 5.3 mg/g catalyst/hr.

The catalyst in this example was made by the impregnation method. A commercial composition of 86% TiO$_2$ and 14% Al$_2$O$_3$ was treated with a saturated solution of zinc nitrate. This was filtered to remove excess zinc nitrate solution, dried at room temperature, and the nitrate decomposed by heating at 250° for 2 hours. This was then followed by heating at 400° overnight to calcine the materials.

EXAMPLE 7

Cerium oxide (3g) was inserted in a tubular reactor and anhydrous ammonia and cyclohexane charged thereto at one atmosphere in the molar ratio of 4 to 1 at a total rate of 60 mmoles per hour. At 550° aniline was produced at a rate corresponding to 1.8 mg/g catalyst/hr.

EXAMPLE 8

Catalyst consisting of 1.5 g of Zn$_3$V$_2$O$_8$ was inserted in a reactor and anhydrous ammonia and cyclohexane charged thereto at one atmosphere in the molar ratio of 4 to 1 at a total rate of 60 mmoles per hour. At 500° aniline was produced at a rate corresponding to 8.6 mg/g catalyst/hr.

EXAMPLES 9-14

A tubular reactor about ½ inch in diameter and 6 inches long (12 × 150 mm) was charged in each of the following examples with catalyst which occupied about a 3 inch section of the reactor. The reactor and catalyst were heated and anhydrous ammonia and cyclohexane were introduced at a 4/1 molar ratio at a rate of 60 mmoles per hour. The product was collected in a cold trap and analyzed by gas chromatography. The results are given in Table II below in which space time yield in mg/g catalyst/hr is given for aniline in column "a" and the weight ratio of benzonitrile to aniline is given in column "b". In all the tables below T indicates a trace of the product was produced and NR indicates no aniline was detected with the GC equipment employed.

TABLE II

| Ex- | | | Temperature | | | | | |
|---|---|---|---|---|---|---|---|---|
| | | | 400° | | 500° | | 600° | |
| ample | Catalyst | Grams | a | b | a | b | a | b |
| 9 | Bi$_4$ZnMo$_3$O$_{16}$ (Scheelite) | 1.7 | NR | | .60 | .05 | 1.1 | .05 |
| 10 | Bi$_4$ZnMo$_3$O$_{16}$ (amorphous) | 1.8 | .15 | 0 | 1.3 | .03 | 2.0 | .21 |
| 11 | 10% PbO/Al$_2$O$_3$ | 2.2 | .35 | 0 | .10 | .87 | .51 | 1.5 |
| 12 | Pb$_2$TiO$_4$ | 4.7 | .05 | .43 | .03 | .93 | .10 | 1.8 |
| 13 | ZnO/ZrO$_2$ | 5.7 | .03 | 0 | .32 | 0 | .29 | .17 |
| 14 | CdO/Al$_2$O$_3$ | 2.3 | — | | .74 | 0 | 1.3 | .70 |

EXAMPLES 15-126

The general procedure of Examples 9-14 was repeated except that the reaction temperatures were varied. Table III gives the results for single component catalysts; Table IV gives the results for two component catalysts; and Table V gives the results for catalysts containing three or four components. In each, column "a" is the space time yield in mg/g catalyst/hr for aniline, column "b" is the weight ratio of benzonitrile to aniline and column "c" is the weight ratio of benzene to aniline.

TABLE III

One Component Catalysts

| | | Temperature | | | | | | | |
|---|---|---|---|---|---|---|---|---|---|
| | | 450° | | | 500° | | | 550° | | |
| Example | Catalyst | a | b | c | a | b | c | a | b | c |
| 15 | CeO₂ | | | | 1.7 | | 20 | 3.6 | 0.12 | 30 |
| 16 | CeO₂ | 0.16 | 0 | | 0.67 | 0 | | 1.8 | 0.08 | |
| 17 | CeO₂ | | | | | | | 1.8 | | |
| 18 | ZnO on carbon | 2.5 | 0 | | 0.73 | 0.05 | | 0.75 | 0.13 | |
| 19 | In₂O₃ | 0.11 | 0 | | 0.43 | 0 | | 0.49 | 0.06 | |
| 20 | Fe₂O₃ | 0.15 | 0 | | 0.79 | 0 | | | | |
| 21 | CdO | 0.40 | 0.18 | | 0.16 | 0.38 | 20 | 0.20 | 1.2 | 100 |
| 22 | FeO | 0.02 | 0 | | | | | T | | |
| 23 | ZnSe | 0.15 | 0 | | 0.16 | 0 | | 0.06 | 0 | |
| 24 | WS₂ | 0.05 | 0 | | 0.12 | 0 | | 0.21 | 0 | |
| 25 | CdS | 0.15 | 0 | | 0.08 | 0 | | 0.02 | 0 | |
| 26 | ZnS | 0.12 | 0 | | 0.05 | 0.19 | | 0.10 | 0.93 | |
| 27 | TiO₂ | T | 2 | | | | | <0.2 | 0.4 | |
| 28 | γ-Al₂O₃ | | | | 0.29 | 0 | | | | |
| 29 | ZrO₂ | | | | 0.13 | 0 | | | | |
| 30 | SnO₂ | | | | | | | (1) | | |
| 31 | ThO₂ | | | | | | | (2) | | |

(1) small amount of aniline produced.
(2) small amount of aniline produced at 600° C.

TABLE IV

TWO COMPONENT CATALYSTS

| | | Temperature | | | | | | | | |
|---|---|---|---|---|---|---|---|---|---|---|
| | | 450° | | | 500° | | | 550° | | |
| Example | Catalyst | a | b | c | a | b | c | a | b | c |
| 32 | Zn/2V oxides | 3.3 | 0.12 | | 14 | 0.05 | | 4.1 | 0.25 | |
| 33 | 3 Zn/2V oxides | 3.3 | 0.10 | | 8.6 | 0.06 | | 5.1 | 0.41 | |
| 34 | Zn/5V oxides | 0.6 | 0 | | 7.6 | 0.04 | | 3.9 | 0.27 | |
| 35 | La/V oxides | | | | 3.1 | 0.06 | 22 | 5.5 | 0.05 | 8.4 |
| 36 | MgMoO₄ | 1 | 0.04 | | 3.1 | 0.03 | 12 | 4.5 | 0.11 | |
| 37 | *3 Zn/2V oxides | 0.76 | 0.16 | | 2.6 | 0.09 | | 9.8 | 0.08 | |
| 38 | Ce/2V oxides | 0.43 | 0 | | 2.4 | 0.01 | | 2.7 | 0.05 | |
| 39 | CdVO₄ | 0.52 | 0 | 10 | 2.2 | 0.01 | 11 | 1.8 | 0.08 | 33 |
| 40 | 3 Co/2V oxides | 0.14 | 0.46 | | 2 | 0.14 | | 3.4 | 0.01 | |
| 41 | EuVO₄ | 0.47 | 0 | | 2 | 0 | | 2.5 | 0.05 | 6.6 |
| 42 | Pb/V oxides | 0.94 | 0.03 | | 2 | 0.04 | | 2.8 | 0.07 | |
| 43 | Ba₃V₂O₈ | 0.18 | 0.11 | | 1.6 | 0.01 | 63 | 2.7 | 0.13 | 16 |
| 44 | 2 Ce/V oxides | 0.27 | 0 | | 1.6 | 0.01 | | 2.6 | 0.05 | |
| 45 | 4 Cu/2V oxides | 0.19 | 0 | | 1.5 | 0 | 19 | 2.5 | 0.08 | 19 |
| 46 | Cd/2V oxides | 0.56 | 0.10 | | 1.4 | 0.10 | | 9.7 | 0.02 | |
| 47 | MnMoO₄ | 0.10 | 0.25 | | 1.3 | 0.08 | | 1.5 | 0.09 | 79 |
| 48 | Gd₂(MoO₄)₃ | 0.13 | 0 | | 1.2 | 0.04 | 6.7 | 1.6 | 0.11 | 26 |
| 49 | ZnMoO₄ | 0.15 | 0.09 | 26 | 1.2 | 0.09 | 44 | 1.2 | 0.62 | 33 |
| 50 | CdS/Al₂O₃ | 2 | 0.01 | | 1.2 | 0.3 | | | | |
| 51 | Zn/Ti oxides | 0.55 | 1.1 | | 1.0 | 1.8 | | 0.89 | 0.84 | |
| 52 | Zn/Ce oxides | 0.87 | 0.02 | | 1.0 | 0.06 | | 1.5 | 0.12 | |
| 53 | Ce₂(MoO₄)₃ | 0.14 | 0 | | 0.53 | 0.03 | 31 | 2.4 | 0.05 | 0 |
| 54 | CdMoO₄ | 0.42 | 0.09 | | 0.88 | 0.03 | 46 | 0.45 | 0.19 | |
| 55 | La₂(MoO₄)₃ | NR | | | | | | 0.96 | | 0 |
| 56 | CeO₂/Al₂O₃ | 0.08 | 0 | | 0.38 | 0.17 | | 0.79 | 1.1 | |
| 57 | 86% TiO₂/14% Al₂O₃ | NR | | | NR | | | 0.25 | 0.11 | |
| 58 | U oxide/Al₂O₃ | NR | | | 0.03 | 0.98 | | 0.43 | 0.50 | |
| 59 | Eu oxide/Al₂O₃ | NR | | | NR | | | 0.16 | 0.79 | |
| 60 | La₂O₃/Al₂O₃ | NR | | | NR | | | 0.05 | 0.26 | |
| 61 | ZnO/Al₂O₃ | 0.03 | 0 | | 0.18 | 0 | | 0.94 | 0.01 | |
| 62 | ZnO/ₙAl₂O₃ | T | | | 0.07 | 0.96 | | | | |
| 63 | 10% CuO/Al₂O₃ | 0.25 | 0.46 | | 0.63 | 0.44 | | 0.60 | 0.34 | |
| 64 | 10% V₂O₅/TiO₂ | 0.45 | 0 | | 0.31 | 0 | | 0.66 | 0.08 | |
| 65 | SnO₂/TiO₂ | T | | | 0.15 | 0 | | 0.30 | 0 | |
| 66 | WO₃/TiO₂ | 0.03 | 0 | | 0.30 | 0.10 | | 0.24 | 0.16 | |
| 67 | 10% PbO/TiO₂ | 0.11 | 0.49 | | 0.20 | 0.14 | | 0.67 | 0.07 | |
| 68 | ZnO/MgO | T | 1.30 | | 0.03 | 1.7 | | 0.10 | 4.4 | |
| 69 | ZnO/silica | 0.45 | 0 | | 0.32 | 0.18 | | 0.18 | 0.15 | |
| 70 | ZnO/ThO₂ | T | | | | | | 0.22 | 0 | |
| 71 | 3Zn/2P oxides | 0.16 | 0 | | 0.14 | 0 | | T | | |
| 72 | Zn/Sb oxides | 0.11 | 0 | | 0.09 | 0 | | T | | |
| 73 | 10% ZnO/CeO₂ | 0.01 | 0.10 | 0.44 | 0.55 | | 1.4 | 0.33 | | |
| 74 | 2% MoO₃/ZnO | 0.16 | 0 | | 0.71 | 0.04 | 2.4 | 1.3 | 0.53 | 13 |
| 75 | 5% WO₃/ZnO | 0.02 | 0 | | 0.32 | 0 | 0.11 | 1.0 | 0.06 | 21 |
| 76 | 6 Ti/Cr oxides | 0.13 | 0 | | 0.34 | 0.12 | | 0.66 | 0.11 | |
| 77 | Cr/Ti oxides | T | | | 0.41 | 0.06 | 0.34 | 0.07 | | |
| 78 | U/3V oxides | 0.05 | 0.65 | | 0.13 | 1.2 | | 0.24 | 0.77 | |
| 79 | 2 Ag/4V oxides | NR | | | NR | | | 0.44 | 13 | |
| 80 | 3 Cu/2V oxides | 0.32 | 9 | | 0.61 | 0 | | 1.4 | 0.08 | |
| 81 | Sr₃V₂O₈ | T | | | | | | 0.72 | 0.10 | |
| 82 | Mg₂V₂O₇ | 0.55 | 0.29 | | 0.26 | 0 | | 0.38 | 0.12 | |
| 83 | Fe/V oxides | 0.07 | 2.6 | | 0.22 | 0.72 | | 0.20 | 0.43 | |
| 84 | HfV₂O₇ | 0.06 | 0.17 | | 0.30 | 0.19 | | 0.12 | 1.1 | |
| 85 | UV₂O₈ | 0.05 | 1.3 | | 0.11 | 0.95 | | 0.12 | 0.94 | |
| 86 | CdSnO₃ | 0.45 | 0.05 | | 0.40 | 0.14 | | 0.24 | | |
| 87 | Zn₂SnO₄ | 0.01 | 0 | | 0.05 | 0 | | 0.12 | 0 | |
| 88 | Ce₂Zr₂O₇ | NR | | | NR | | | 0.10 | 0.22 | |
| 89 | Zn/2Fe oxides | T | | | 0.15 | 0.06 | | 0.83 | 0.01 | |
| 90 | CdVO₄ | 0.52 | 0 | 10 | 2.2 | 0.01 | 11 | 1.8 | 0.08 | 33 |

TABLE IV-continued

TWO COMPONENT CATALYSTS

| | | Temperature | | | | | | | | |
|---|---|---|---|---|---|---|---|---|---|---|
| | | 450° | | | 500° | | | 550° | | |
| Example | Catalyst | a | b | c | a | b | c | a | b | c |
| 91 | P/10Mo oxides | NR | | | | 0.61 | 0.35 | | | |
| 92 | 5% MoO$_3$/CeO$_2$ | 0.01 | 2.0 | | 0.12 | 0.04 | 146 | 0.78 | 0.02 | |
| 93 | Sn/V oxides | 0.13 | 0.29 | | 0.42 | 0.13 | | 0.88 | 0.06 | |

*This catalyst was prepared by the precipitation method. An aqueous solution of zinc nitrate was added to an aqueous solution of ammonium vanadate with the molar ratio of zinc to vanadium of 3:2. A yellow precipitate formed which was filtered, air dried and calcined at 250° for 3 hours and then at 400° overnight.

TABLE V

Three or More Component Catalysts

| | | Temperature | | | | | | | | |
|---|---|---|---|---|---|---|---|---|---|---|
| | | 450° | | | 500° | | | 550° | | |
| Example | Catalyst | a | b | c | a | b | c | a | b | c |
| 94 | 0.05 Cd/Zn/2V oxides | 1.8 | 0.17 | 31 | 14.5 | 0.02 | 2.3 | 35.9 | 0.06 | 1.5 |
| 95 | 0.20 P/Zn/2V oxides | 0.84 | 0.19 | | 11.5 | 0.03 | 7 | 10.6 | 2.6 | 4 |
| 96 | 0.40 Mg/Zn/2V oxides | 1.5 | 0.26 | | 10.6 | 0.09 | 4.1 | 5.8 | 0.55 | 11 |
| 97 | 0.05 Ce/Zn/2V oxides | 0.06 | 1.2 | | 5.4 | 0.05 | 6.9 | 14.8 | 0.06 | 1.2 |
| 98 | 0.20 La/Zn/2V oxides | 0.10 | 0.96 | | 4.7 | 0.08 | 6.1 | 5.4 | 0.07 | |
| 99 | Ti/Zn/Al oxides | 5.3 | 0.04 | | 4.0 | 0.11 | | 1.1 | 0.35 | |
| 100 | NiSnV$_2$O$_8$ | 0.26 | 0.53 | | 3.8 | 0.03 | 7.8 | 2.2 | 0.04 | 32 |
| 101 | CdMoO$_4$/Al$_2$O$_3$ | 1.8 | 0 | | 3.6 | 0 | 14 | 1.4 | 0.04 | |
| 102 | 4 Ti/Mg/Zn oxides | 1.5 | 0.05 | | 3.5 | 0.06 | 6.7 | 8.7 | 0.24 | |
| 103 | Ce/Zn/V oxides | 0.78 | 0.04 | 0.91 | 3.3 | 0.02 | 0.5 | 4.3 | 0.09 | 1 |
| 104 | 4 Ti/La/Zn oxides | 0.22 | 0.1 | | 1.8 | 0.1 | 33 | 5.5 | 0.37 | 22 |
| 105 | Ti/Zn/Al oxides | 0.4 | 0 | | 1.6 | 0.03 | | 2.8 | 0.12 | |
| 106 | 4 Ti/Zn/Al oxides | 0.27 | 0 | | 1.3 | 0.08 | | 1.7 | 0.67 | |
| 107 | Ca/Mo/Al oxides | 0.65 | 0 | | 1.4 | 0.05 | | 1.1 | 0.34 | |
| 108 | CdS/TiO$_2$/Al$_2$O$_3$ | 2.5 | 0.01 | | 1.3 | 0.28 | | | | |
| 109 | CdS/ZnS/Al$_2$O$_3$ | 2.4 | 0.02 | | 1.3 | 0.35 | | | | |
| 110 | CuMoO$_4$/Al$_2$O$_3$ | 0.44 | | | 1.3 | 0.05 | 26 | 0.79 | 0.47 | |
| 111 | Ce$_2$(MoO$_4$)$_3$/Al$_2$O$_3$ | 1.6 | 0.06 | | 1.2 | 0.15 | 40 | 0.28 | 1.2 | 100 |
| 112 | La$_2$(MoO$_4$)$_3$/Al$_2$O$_3$ | 0.22 | 0 | | 1.1 | 0.04 | 21 | 0.87 | 0.17 | |
| 113 | CdO/TiO$_2$/Al$_2$O$_3$ | 0.15 | 0 | | 1.1 | 0 | | 9.8 | 0.006 | |
| 114 | Rare earth oxides/TiO$_2$/Al$_2$O$_3$ | 0.16 | 0.16 | | 0.67 | 0.60 | | | | |
| 115 | V$_2$O$_5$/TiO$_2$Al$_2$O$_3$ | 0.46 | 0.04 | | 0.46 | 0.07 | | 0.91 | 0.11 | |
| 116 | Pb/Mo/Al oxides | 1.1 | 0 | | 0.43 | 0.10 | | 0.84 | 0.11 | |
| 117 | CeO$_2$/TiO$_2$/Al$_2$O$_3$ | T | | | 0.25 | 0.11 | | 0.50 | 0.08 | |
| 118 | CuCeV$_2$O$_8$ | 0.30 | 0 | | 0.23 | 0 | | 0.11 | 0 | |
| 119 | FeTiO$_3$ + TiO$_2$ | 0.05 | 0.10 | | 0.10 | 0.26 | | 0.13 | 0.38 | |
| 120 | ZnO/Al$_2$O$_3$/ZrO$_2$ | 0.07 | 0 | | 0.10 | 0 | | 0.20 | 0.03 | |
| 121 | MgO/Al$_2$O$_3$/TiO$_2$ | 0.05 | 0 | | 0.08 | 0 | | 0.11 | 0.23 | |
| 122 | Cr$_2$O$_3$/Al$_2$O$_3$/TiO$_2$ | 0.12 | 0 | | | | | 0.45 | 0.03 | |
| 123 | Fe$_2$O$_3$/Al$_2$O$_3$/TiO$_2$ | 0.01 | 0 | | | | | 0.83 | 0.01 | |
| 124 | Ce$_2$Zr$_2$O$_7$ | NR | | | NR | | | 0.10 | 0.22 | |
| 125 | Zn/Ce/TiO$_2$/Al$_2$O$_3$ | 0.29 | 0 | | 2.0 | 0.07 | | 4.5 | 0.28 | |
| 126 | ZnO/V$_2$O$_5$/TiO$_2$/Al$_2$O$_3$ | 0.92 | 0 | | 1.6 | 0.02 | | 2.1 | 0.09 | |

EXAMPLES 127-129

A quartz tube (25 × 300 mm) was charged with a 25 mm long section of catalyst and 90 mm section of silicon carbide (serving as heat exchanger). Ammonia gas and cyclohexane were introduced at a rate of 9.82 × 10$^{-3}$ and 1.97 × 10$^{-3}$ mole per minute respectively at 1 atm. pressure with a contact time of between ¼ and ½ sec.

The effluent product was collected in a trap maintained at about 0° C. and analyzed by vapor phase chromatography (20% Carbowax 20 M ® plus 4% alcoholic KOH on 80/100 mesh Chromosorb "W" HP ®. The above trademarks are owned by Union Carbide Co. and Johns Manville Co., respectively.) The following table shows the catalyst, the temperature, and the amounts of aniline and benzene produced as a percent of the liquid collected.

TABLE VI

| Example | Catalyst | Temp. °C | %C$_6$H$_5$NH$_2$ | %C$_6$H$_6$ |
|---|---|---|---|---|
| 127 | SrO/MoO$_3$/Al$_2$O$_3$ | 500 | 0.9 | 1.1 |
| 128 | CaO/MoO$_3$/Al$_2$O$_3$ | 480 | 1.4 | 1.76 |
| 129 | ZnO/MoO$_3$/Al$_2$O$_3$ | 480 | 1.72 | 3.3 |

EXAMPLE 130

When the procedure of Examples 127-129 was employed using a metal reactor tube with ZnO/Al$_2$O$_3$ as catalyst at 550° at 4 atm. pressure, there was obtained a liquid product of which 1.14% was aniline and 4.3% was benzene.

EXAMPLE 131

When the procedure of Examples 127-129 was used with ZnO/Al$_2$O$_3$ at 550° and the contact time increased to 2 seconds, there was obtained about 2% of aniline and 7% benzene in the liquid product.

EXAMPLES 132-139

A quartz tube (25 × 300 mm) was charged with a 25 mm long section of catalyst and a 90 mm section of silicon carbide. Ammonia gas and cyclohexane were introduced at rates of 3 × 10$^{-3}$ mole and 7.5 × 10$^{-4}$ mole per minute at a reaction temperature of 500° C. The following Table VII shows the catalyst and amounts of aniline and benzene obtained in the liquid product. (In the table, a square indicates a vacancy in catalyst structure.)

TABLE VII

| Example | Catalyst | %C₆H₅NH₂ | %C₆H₆ |
|---|---|---|---| benzene, and benzonitrile, and the total amount of product collected in 20 minutes are shown in Table VIII. In each case the volume of catalyst used was 10 ml.

TABLE VIII

| Example | Catalyst | %C₆H₅NH₂ | %C₆H₆ | %C₆H₅CN | Total Product (g) |
|---|---|---|---|---|---|
| 140 | 3ZnO/CeO₂/TiO₂/Al₂O₃ | 3.8 | 2.1 | 0.08 | 0.85 |
| 141 | Bi₂O₃(2%)/ZnO(21%)/TiO₂/Al₂O₃ | 3.8 | 3.7 | 0.19 | 1.1 |
| 142 | CaO(2%)/ZnO(21%)/TiO₂/Al₂O₃ | 3.1 | 2.5 | 0.14 | 1.02 |
| 143 | ZrO₂/CeO₂/MoO₃/TiO₂/Al₂O₃ | 2.7 | 10.9 | 0.21 | 0.3 |
| 144 | Y₂O₃(2%)/ZnO(21%)/TiO₂/Al₂O₃ | 2.44 | 1.1 | 0.004 | 1.02 |
| 145 | CeO₂(2%)/ZnO(21%)/TiO₂/Al₂O₃ | 2.4 | 1.4 | 0.02 | 0.9 |
| 146 | PbO(2%)/ZnO(21%)/TiO₂/Al₂O₃ | 2.3 | 2.8 | 0.13 | 1.0 |
| 147 | SrO(2%)/ZnO(21%)/TiO₂/Al₂O₃ | 2.2 | 0.71 | 0.04 | 1.01 |
| 148 | CdO(2%)/ZnO(21%)/TiO₂/Al₂O₃ | 2.2 | 1.3 | 0.02 | 0.9 |
| 149 | CoO(2%)/ZnO(21%)/TiO₂/Al₂O₃ | 2.1 | 12.7 | 0.22 | 1.4 |
| 150 | MgO(2%)/ZnO(21%)/TiO₂/Al₂O₃ | 2.0 | 2.6 | 0.06 | 1.02 |
| 151 | Sm₂O₃(2%)/ZnO(21%)TiO₂/Al₂O₃ | 2.0 | 1.14 | 0.05 | 1.6 |
| 152 | La₂O₃(2%)/ZnO(21%)/TiO₂/Al₂O₃ | 1.9 | 1.0 | 0.06 | 0.9 |
| 153 | LaMoO₄/Al₂O₃ | 1.83 | 12.1 | 0.08 | — |
| 154 | ThO₂(2%)/ZnO(21%)/TiO₂/Al₂O₃ | 1.78 | 1.78 | 0.04 | 0.9 |
| 155 | RuO₂(2%)/ZnO(21%)/TiO₂/Al₂O₃ | 1.7 | 1.8 | 0.07 | 0.5 |
| 156 | Zr₀.₈₈Ce₀.₀₈MoO₄/Al₂O₃ | 1.6 | 5.1 | 0.0 | 0.7 |
| 157 | PbO/CeO₂/MoO₃TiO₂/Al₂O₃ | 1.5 | 7.5 | — | 0.9 |
| 158 | CaO/Bi₂O₃/MoO₃/TiO₂/Al₂O₃ | 1.5 | 3.2 | — | 0.5 |
| 159 | ZnO/CeO₂/MoO₃/TiO₂/Al₂O₃ | 1.5 | 10.2 | 0.03 | 0.83 |
| 160 | Yb₂O₃(2%)/ZnO(21%)/TiO₂/Al₂O₃ | 1.5 | 1.3 | 0.01 | 0.6 |
| 161 | PbO/Bi₂O₃/MoO₃/TiO₂/Al₂O₃ | 1.42 | 14.2 | — | 1.0 |
| 162 | ZnO/Bi₂O₃/MoO₃/TiO₂/Al₂O₃ | 1.4 | 15.1 | — | 1.0 |
| 163 | CeO₂/MoO₃/Al₂O₃ | 1.35 | 4.9 | 0.04 | 1.0 |
| 164 | Zn₀.₈₈Bi₀.₀₈□₀.₀₄MoO₄/Al₂O₃ | 1.3 | 3.7 | 0.06 | 1.0 |
| 165 | Ca₀.₈₈Ce₀.₀₈MoO₄/Al₂O₃ | 1.33 | 2.7 | 0.019 | 0.90 |
| 166 | Pb/Bi/Mo/Oxides/Al₂O₃ | 1.33 | 6.5 | 0.015 | 1.2 |
| 167 | CeO₂/MoO₃/TiO₂/Al₂O₃ | 1.3 | 13.6 | 0.03 | 1.1 |
| 168 | AgO(2%)/ZnO(21%)/TiO₂/Al₂O₃ | 1.3 | 3.2 | 0.03 | 0.9 |
| 169 | Sm₂O₃/MoO₄/Al₂O₃ | 1.22 | 7.4 | 0.02 | 0.93 |
| 170 | Zn₀.₇₆Ce₀.₁₆MoO₄/Al₂O₃ | 1.2 | 3.0 | 0.0 | 0.78 |
| 171 | Mixed rare earth oxides/MoO₃/Al₂O₃ | 1.16 | 1.43 | 0.0 | 0.90 |
| 172 | PbO/La₂O₃/MoO₃/TiO₂/Al₂O₃ | 1.1 | 45 | — | 1.0 |
| 173 | 2ZnO/CeO₂/TiO₂ | 1.1 | 1.5 | 0.03 | 1.0 |
| 174 | Pb₀.₆₄Ce₀.₂₄MoO₄/Al₂O₃ | 1.1 | 1.14 | 0.02 | 0.84 |
| 175 | Er₂O₃/MoO₃/Al₂O₃ | 1.12 | 2.2 | 0.04 | 0.91 |
| 176 | PbO/CeO₂/MoO₃/Al₂O₃ | 1.0 | 3.5 | 0.0 | 1.0 |
| 177 | ZnO/Bi₂O₃/MoO₃/Al₂O₃ | 1.0 | 7.1 | 0.03 | 0.6 |
| 178 | PbO/La₂O₃/MoO₃/Al₂O₃ | 1.0 | 3.3 | 0.04 | 1.0 |
| 179 | CaO/CeO₂/MoO₃/TiO₂/Al₂O₃ | 1.0 | 5.5 | 0.13 | 0.9 |
| 180 | Pr₂O₃(2%)/ZnO(21%)/TiO₂/Al₂O₃ | 1.02 | 0.65 | 0.0 | 0.9 |
| 181 | Y₂O₃/MoO₃/Al₂O₃ | 0.99 | 1.77 | 0.04 | 0.80 |
| 182 | Cu/As/V/oxides | 0.88 | 6.9 | 0.01 | — |
| 183 | 10% ZnO/2% CdO/TiO₂ | 0.86 | 5.0 | 0.07 | 0.94 |
| 184 | CaO/Bi₂O₃/MoO₃/Al₂O₃ | 0.9 | 1.4 | 0.02 | 1.0 |
| 185 | Fe₂O₃(2%)/ZnO(21%)/TiO₂/Al₂O₃ | 0.88 | 6.0 | 0.0 | 1.6 |
| 186 | 0.1ZnO/0.01CdO/TiO₂ (0.9) | 0.8 | 5.9 | 0.08 | 0.95 |
| 187 | CuO(2%)/ZnO(21%)/TiO₂/Al₂O₃ | 0.64 | 5.8 | 0.0 | 1.4 |
| 188 | Cr₂O₃(2%)/ZnO(21%)/TiO₂/Al₂O₃ | 0.62 | — | 0.12 | 0.96 |
| 189 | Bi₂O₃/MoO₃/TiO₂ | 0.76 | 0.75 | 0.009 | 0.92 |
| 190 | In₂O₃/MoO₃/Al₂O₃ | 0.77 | 4.3 | 0.0 | 0.95 |
| 191 | 17.6 Bi₂O₃/12.5 MoO₃/69.8 TiO₂ (wt. %) | 0.7 | 5.1 | 0.03 | 1.0 |
| 192 | Bi₂O₃/MoO₃/TiO₂/Al₂O₃ | 0.23 | 0.14 | 0.0 | 1.0 |
| 193 | Fe₂O₃/Al₂O₃ | 0.28 | 9 | 0.0 | 1.0 |
| 194 | ZnO/TiO₂/Al₂O₃/Nb₂O₅ | 0.2 | 1.32 | 0.0 | 0.74 |
| 195 | Cerium metatungstate/Al₂O₃ | 0.09 | 0.37 | 0.0 | 0.82 |
| 196 | Lanthanum metatungstate/Al₂O₃ | 0.05 | 0.081 | 0.0 | 0.93 |
| 197 | ZnO/TiO₂(rutile) | 0.06 | 0.1 | 0.0 | 0.85 |
| 198 | ZnO/1.47 TiO₂/0.147 CeO₂ | 0.05 | 0.04 | 0.0 | 0.95 |
| 199 | PbO/WO₃/Al₂O₃ | 0.1 | 0.67 | 0.0 | 1.0 |
| 200 | CaO/WO₃/Al₂O₃ | 0.05 | 0.08 | 0.0 | 1.2 |
| 201 | La₂O₃/WO₃/Al₂O₃ | 0.03 | 0.04 | 0.0 | 1.0 |
| 202 | Bi₄Ti₃O₁₂ | 0.06 | 2.6 | 0.0 | 1.4 |
| 203 | 19% MnO₂/Al₂O₃ | 0.08 | 0.65 | 0.0 | — |
| 204 | Re/Ti/Al oxides | 0.06 | 25 | 0.0 | 0.8 |
| 205 | TeO₂/TiO₂/Al₂O₃ | 0.095 | 6.0 | 0.0 | 1.0 |
| 206 | 21% ZnO/TiO₂ | 0.3 | 3.2 | 0.04 | 1.0 |
| 207 | 2% NiO/21% ZnO/TiO₂/Al₂O₃ | 0.3 | 3.0 | 0.01 | 0.9 |
| 208 | Ni₂V₂O₇ . V₂O₅ | 0.21 | 50 | 0.15 | 0.63 |

| 132 | Pb/Mo/oxides | 0.6 | 1.0 |
| 133 | Pb.₈₈La.₀₈□.₀₄MoO₄ | 1.33 | 4.0 |
| 134 | Pb.₇₆Ce.₁₆□.₀₈MoO₄/Al₂O₃ | 1.8 | 2.4 |
| 135 | Pb.₈₈La.₀₈□.₀₄MoO₄/Al₂O₃ | 1.17 | 1.8 |
| 136 | Cu.₈₈Bi.₀₈□.₀₄MoO₄/Al₂O₃ | .32 | .85 |
| 137 | MoO₃/TiO₂ | .46 | 5.6 |
| 138 | Ca.₇₆Bi.₁₆□.₀₈MoO₄/Al₂O₃ | 1.03 | 1.04 |
| 139 | Pb.₈₈Bi.₀₄□.₀₄MoO₄/Al₂O₃ | 1.12 | 1.5 |

EXAMPLES 140-208

The general procedure of Examples 132-139 was repeated. The catalyst, the relative amounts of aniline,

EXAMPLES 209-222

The general procedure of Examples 132-139 was repeated at different temperatures. In each catalyst the amount of vanadium oxide was 10% by weight based on the aluminum oxide and the remaining metal oxide was in equimolar proportion to the vanadium oxide. The results obtained are given in Table IX below.

TABLE IX

| Example No. | Catalyst: Oxides of | Temperature | | | | | |
|---|---|---|---|---|---|---|---|
| | | 450° | | 500° | | 550° | |
| | | % Aniline | % Benzene | % Aniline | % Benzene | % Aniline | % Benzene |
| 209 | Mg/V/Al | 0.32 | 3.0 | 0.5 | 1.5 | 0.6 | 9.9 |
| 210 | Ca/V/Al | 0.13 | 0.25 | 0.8 | 0.3 | 1.1 | 3.0 |
| 211 | Sr/V/Al | 0.28 | 0.46 | 1.3 | 3.0 | 1.9 | 12.7 |
| 212 | Ba/V/Al | 0.2 | 0.0 | 0.8 | 0.8 | 1.3 | 20.4 |
| 213 | Y/V/Al | 0.2 | 0.0 | 0.8 | 0.5 | 1.7 | 4.1 |
| 214 | La/V/Al | 0.1 | 0.3 | 0.7 | 0.7 | 2.1 | 2.5 |
| 215 | Zr/V/Al | 0.0 | 0.4 | 0.4 | 0.1 | 0.1 | 2.4 |
| 216 | Cu/V/Al | 0.2 | 6.0 | 0.6 | 2.1 | 0.8 | 9.1 |
| 217 | Zn/V/Al | 0.1 | 2.3 | 3.1 | 0.1 | 0.7 | 11.7 |
| 218 | Ag/V/Al | 0.3 | 2.7 | 0.5 | 10.4 | 0.5 | 35.2 |
| 219 | Cd/V/Al | 0.2 | 0 | 1.6 | 4.8 | 0.9 | 7.4 |
| 220 | Ga/V/Al | 0.9 | 0.7 | 1.0 | 0.8 | 0.7 | 11.4 |
| 221 | In/V/Al | 1.0 | 2.3 | 1.8 | 6.7 | 1.6 | 11.0 |
| 222 | Pb/V/Al | 0.8 | 0.4 | 1.3 | 3.5 | 1.3 | 12.3 |

EXAMPLE 223

A. A catalyst was prepared by thoroughly mixing together

| Compound | Grams |
|---|---|
| Al(NO$_3$)$_3$ . xH$_2$O | 17.4 |
| CdNO$_3$ . xH$_2$O | 4.8 |
| Ce(NO$_3$)$_3$ . xH$_2$O | 5.3 |
| Fe(NO$_3$)$_3$ . xH$_2$O | 11.5 |
| In$_2$O$_3$ | 2.8 |
| SnO$_2$ | 3.0 |
| ThO$_2$ | 2.0 |
| TiO$_2$ | 2.0 |
| Zn(NO$_3$)$_2$ . xH$_2$O | 7.3 |
| ZrO(NO$_3$)$_2$ . xH$_2$O | 4.4 |
| Water | 150.0 |

The resultant slurry-solution was evaporated to dryness on a hot plate. The solids were calcined for a total of 7 hours at the following temperatures and in the sequence shown:

| ° C | Hours |
|---|---|
| 200 | 1 |
| 300 | 1 |
| 400 | 1 |
| 500 | 4 |

The catalyst was then ground to 10–20 mesh.

B. Aniline was made from cyclohexane using the above catalyst as follows. A three inch section of a Vycor ® tubular reactor having a 0.5 inch inside diameter was loaded with 5 g of the catalyst. Anhydrous ammonia was then passed through the reactor while the temperature of the reactor and its contained catalyst was raised to 525° C. When all the water adsorbed on the catalyst had been evaporated off, the ammonia flow was adjusted to a rate of 21 ml per minute and a flow of cyclohexane at 2 ml per hour was started. The effluent was collected in a zero degree cold trap for 30 minutes and the collected liquid analyzed by GC using a dual column system of 5 feet × ⅛ inch Carbowax ® 20 M and 5 feet × ⅛ inch UCW-98 (silicone polymer containing methyl and vinyl groups) dispersed on Chromsorb W at 180° C. Aniline with a retention time of 11.4 minutes was detected whereas benzonitrile with a retention time of 8.8 minutes was not detected.

We claim:

1. The process which consists essentially in heating a starting hydrocarbon of the formula

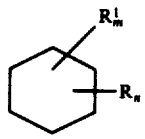

wherein
R and R$^1$ are alkyl of 1–4 carbon atoms and
m and n are 0 or 1 with anhydrous ammonia at a temperature range of 300°–650° C in the absence of air to produce a compound of the formula

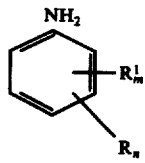

where R, R$^1$, m and n have the values stated above and where the heating is carried out in the presence of a catalyst selected from the group consisting of:

A. one or more oxides of Al, Cd, Ce, Fe, In, Sn, Th, Ti, Zn and Zr;

B. vanadium oxide and one or more oxides of Ag, As, Ba, Ca, Cd, Ce, Co, Cu, Eu, Fe, Gd, Hf, In, La, Mg, Mn, Ni, P, Pb, Sb, Sn, Sr, Ti, U and Zn;

C. titanium oxide and one or more oxides of Bi, Cr, Cu, Mo, Pb, U and W;

D. zinc oxide and one or more oxides of Cr, La, Mg, P, Si, Sb, W and the pair Bi-Mo;

E. aluminum oxide and one or more oxides of Cu, Eu, La, Mn, Pb, and U;

F. aluminum oxide, molybdeum oxide and one or more oxides of Ca, Cd, Ce, Cu, Er, Fe, In, La, Ni, Pb, Sm, Sr, Ti, U, Y and Zn;

G. aluminum oxide, tungsten oxide and one or more oxides of Ca, Ce, Cu, Fe, In, La, Pb, Sm, Ti, U and Zn;

H. aluminum oxide, titanium oxide and one or more oxides of Cr, Mg, rare earths, Re, Te and V;

I. aluminum oxide, titanium oxide, zinc oxide and one or more oxides of Ag, Bi, Ca, Co, Cr, Cu, Hg, La, Mg, Nb, Ni, Pb, Pr, Ru, Sm, Sr, V, Yb, and Y;

J. aluminum oxide, molybdenum oxide, bismuth oxide and one or more oxides of Ca, Cu, Pb, Ti, and Zn;

K. aluminum oxide, molybdenum oxide, zirconium oxide and one or more oxides of Ce, Ti, and Zn;

L. molybdenum oxide and one or more oxides of Cd, Ce, Cu, Fe, Gd, La, Mg, Mn, Nb, P, Pb, Ti and Zn;

M. zinc oxide, titanium oxide and one or more oxides of Cr, La, Mg and Nb;

N. CdS; CoS; CdS/aluminum oxide; CdS/titanium oxide/aluminum oxide; chromium sulfide; ZnSe; ZnS; ZnTe; ZnS/aluminum oxide; CdS/ZnS/aluminum oxide and $WS_2$; and O. aluminum oxide, vanadium oxide and one or more oxides of Ag, Ba, Ca, Cd, Cu, Ga, In, La, Mg, Pb, Sr, Y, Zn, and Zr.

2. The process of claim 1 in which the starting hydrocarbon is cyclohexane.

3. The process of claim 1 in which the temperature range is 400°-600° C.

4. The process of claim 1 in which the temperature range is 450°-550° C.

5. The process of claim 1 in which the reactants are in contact with the catalyst at the reaction temperature for about 0.1 second to about 10 minutes.

6. The process of claim 1 in which the reactants are in contact with the catalyst at the reaction temperature for about 1 second to about 8 minutes.

7. The process of claim 1 in which the molar ratio of the starting hydrocarbon to ammonia ranges from 5/1 to 1/10.

8. The process of claim 1 in which the catalyst is selected from group A.

9. The process of claim 1 in which the catalyst is selected from group B.

10. The process of claim 1 in which the catalyst is selected from group C.

11. The process of claim 1 in which the catalyst is selected from group D.

12. The process of claim 1 in which the catalyst is selected from group E.

13. The process of claim 1 in which the catalyst is selected from group F.

14. The process of claim 1 in which the catalyst is selected from Group G.

15. The process of claim 1 in which the catalyst is selected from group H.

16. The process of claim 1 in which the catalyst is selected from group I.

17. The process of claim 1 in which the catalyst is selected from group J.

18. The process of claim 1 in which the catalyst is selected from group K.

19. The process of claim 1 in which the catalyst is selected from group L.

20. The process of claim 1 in which the catalyst is selected from group M.

21. The process of claim 1 in which the catalyst is selected from group N.

22. The process of claim 1 in which the catalyst is selected from group O.

23. The process of claim 1 in which a member of group A or vanadium oxide comprises half or more of the catalyst.

24. The process of claim 1 in which the catalyst contains zinc oxide and titanium oxide.

25. The process of claim 1 in which the catalyst contain zinc oxide and vanadium oxide.

26. The process of claim 1 in which the catalyst contains zinc oxide and titanium oxide and one or more oxides of the group aluminum, cadmium, cerium, lanthanum and thorium.

27. The process of claim 1 in which the catalyst is aluminum oxide/titanium oxide/zinc oxide/cerium oxide.

28. The process of claim 1 in which the catalyst is aluminum oxide/titanium oxide/zinc oxide/cadmium oxide.

29. The process of claim 1 in which the catalyst is zinc oxide/titanium oxide/cerium oxide.

30. The process of claim 1 in which the catalyst is zinc oxide/titanium oxide/lanthanum oxide.

31. The process of claim 1 in which the catalyst is aluminum oxide/molybdenum oxide/zirconium oxide/cerium oxide/titanium oxide.

32. The process of claim 1 in which the catalyst is aluminum oxide/molybdenum oxide and one or more oxides of the group consisting of calcium, lead and rare earths.

33. The process of claim 1 in which the catalyst is aluminum oxide/molybdenum oxide/cerium oxide/lead oxide.

34. The process of claim 1 in which the catalyst is cadmium sulfide/zinc sulfide/aluminum oxide.

35. The process of claim 1 in which the catalyst is zinc oxide, vanadium oxide and aluminum oxide.

36. The process of claim 1 in which the catalyst is zinc oxide, vanadium oxide and cadmium oxide.

37. The process of claim 1 in which the catalyst is zinc oxide, vanadium oxide and cerium oxide.

38. The process of claim 1 in which the catalyst is zinc oxide, vanadium oxide and lanthanum oxide.

* * * * *